(12) United States Patent
Warner et al.

(10) Patent No.: US 8,653,303 B2
(45) Date of Patent: Feb. 18, 2014

(54) PROCESSES FOR PREPARING ACETIC ANHYDRIDE

(75) Inventors: R. Jay Warner, Houston, TX (US); Melchoir Meilchen, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 106 days.

(21) Appl. No.: 13/359,060

(22) Filed: Jan. 26, 2012

(65) Prior Publication Data

US 2013/0197267 A1 Aug. 1, 2013

(51) Int. Cl.
*C07C 51/54* (2006.01)

(52) U.S. Cl.
USPC ........................................................ 562/892

(58) Field of Classification Search
USPC .................... 562/888, 892, 896, 887
See application file for complete search history.

(56) References Cited

U.S. PATENT DOCUMENTS

| | | | |
|---|---|---|---|
| 3,111,548 A * | 11/1963 | Altenschopfer et al. | 560/172 |
| 4,107,002 A | 8/1978 | Eck et al. | |
| 5,281,359 A * | 1/1994 | Scates et al. | 252/182.16 |
| 2006/0041162 A1 * | 2/2006 | Warner | 560/1 |

OTHER PUBLICATIONS

Agreda et al. (Acetic acid and Its Derivatives, p. 149, 1993, downloaded from the internet on Jun. 6, 2013).*
Spes (Chemical Reactions in Liquid Ring Pumps, Chemie Ing. Techn vol. 38 1966).*
Spes (Chemical Reactions in Liquid Ring Pumps, Chemie Ing. Techn vol. 38 1966) English translation of Spes was conducted by Schreiber Translations, Inc. Oct. 2013.*

* cited by examiner

*Primary Examiner* — Wu-Cheng Winston Shen
*Assistant Examiner* — Blaine G Doletski

(57) ABSTRACT

In one embodiment, the invention is to a process for producing acetic anhydride. The process includes at least a step of carbonylating methanol and/or a methanol derivative with carbon monoxide to form acetic acid, and contacting ketene with the acetic acid to form a crude acetic anhydride product stream and a vent stream having unreacted ketene. The process further comprises a step of directing at least a portion of the vent stream to a liquid ring vacuum compressor having a ring seal fluid comprising acetic acid The unreacted ketene in the portion of the vent stream contacts the ring seal fluid to form supplemental acetic anhydride.

22 Claims, 1 Drawing Sheet

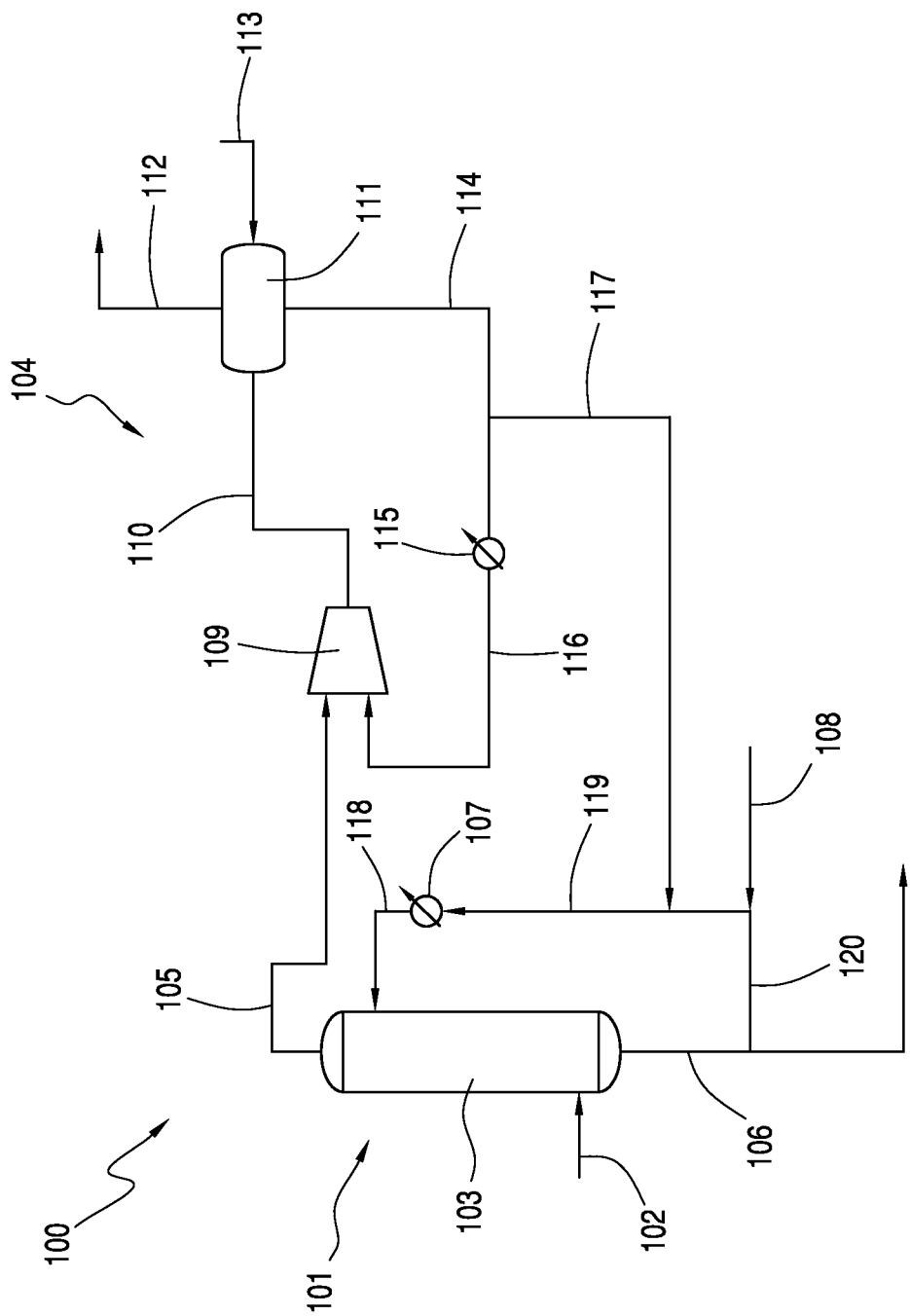

PROCESSES FOR PREPARING ACETIC ANHYDRIDE

FIELD OF THE INVENTION

The present invention relates generally to the production of acetic anhydride. More specifically, the present invention relates to the production of crude acetic anhydride acid via the reaction of acetic acid and ketene, and the subsequent conversion of unreacted ketene to acetic anhydride.

BACKGROUND OF THE INVENTION

Acetic anhydride is a clear, colorless, liquid with a sharp, vinegar-like odor. Acetic anhydride is a commercially valuable chemical and can be found in a wide variety of industrial applications. Some primary applications of acetic anhydride include its use in the manufacture of cellulose acetate for films, plastic goods and coatings. Other applications include use in the manufacture of perfumes, explosives, synthetic fibers, sweeteners, polymers (e.g., polyoxytetramethylene glycol and polyacetal), weed killers, fungicides, various industrial chemicals, acetylsalicylic acid (aspirin), acetylcholine hydrochloride, acetophenacetin, sulfonamides, aceto-p-aminophenol, cortisone, acetanilide, theophylline, sulfa drugs, certain vitamins and hormones, and many other various pharmaceuticals and pharmaceutical intermediates not listed here. Acetic anhydride can also be used in the chemical treatment of papers and textiles and to produce acetyl ricinoleates, triacetin, acetyl tributyl citrate, and other plasticizers. Because acetic anhydride reacts with water, it is also sometimes used as a dehydrating agent in reaction mixtures where the removal of water is necessary.

It is known that acetic anhydride can be prepared via the reaction of acetic acid and ketene. Ketene, a valuable intermediate for the synthesis of many organic compounds, may be prepared by the thermal decomposition (continuous cracking) of acetic acid in the presence of a catalyst, e.g., triethyl phosphate. This reaction may be conducted at temperatures at or above 600° C. and under pressures ranging from about 10 to 50 kPa. Ammonia may be added to the mixture of hot cracked gas shortly after it leaves the reaction zone to neutralize the catalyst. Ketene is then isolated from the cracked gas and reacted with excess acetic acid to obtain crude acetic anhydride.

Typically, the ketene/acetic acid reaction is carried out in a system which includes an absorber and a scrubber. The majority of the ketene is reacted in the absorber stage. A crude acetic anhydride product stream exits the bottom of the absorber. Residual ketene, e.g., unreacted ketene, exits the absorber stage (via overhead gas stream) and is typically directed to a scrubber to convert the unreacted ketene into additional acetic anhydride. Although this process has been widely adopted throughout industry, the process requires the use of both an absorber and a scrubber to achieve the desired overall ketene conversion. These components, unfortunately, represent significant capital expenditures. Also, the continuous operation of these components leads to increased energy requirements for the process as a whole.

Thus, notwithstanding the above, there remains a need for processes for preparing acetic anhydride which both ease the burden of capital expenditures associated with existing processes, and offer high ketene efficiency and product yield. The present invention addresses these and other needs by providing processes for preparing acetic anhydride that utilizes a liquid ring vacuum compressor to react residual ketene exiting the reactor at significantly lower costs and increased efficiency.

BRIEF DESCRIPTION OF DRAWINGS

The invention is described in detail below with reference to the appended drawings, wherein like numerals designate similar parts.

FIG. 1 is a process flowsheet showing an acetic anhydride reactor system in accordance with an embodiment of the present invention.

SUMMARY OF THE INVENTION

In one embodiment, the invention is to a process for producing acetic anhydride. The process comprises the step of carbonylating methanol and/or a methanol derivative with carbon monoxide to form acetic acid. The acetic acid is then contacted with ketene to produce a crude acetic anhydride product stream comprising acetic anhydride and a vent stream comprising unreacted ketene. Preferably, the contacting is performed in an absorber column. The process further comprises the step of directing at least a portion of the vent stream to a liquid ring vacuum compressor comprising a ring seal fluid comprising acetic acid. The unreacted ketene is then contacted with the ring seal fluid to form supplemental acetic anhydride product. In embodiments, the overall ketene efficiency is at least 98%. In one embodiment, the inventive process further comprises the step of separating the supplemental acetic anhydride product to form a recycle stream comprising acetic acid and a decomposition stream. In another embodiment, at least a portion of the crude acetic anhydride product stream is hydrogenated to form ethanol.

DETAILED DESCRIPTION OF THE INVENTION

Introduction

The production of acetic anhydride via the reaction between acetic acid and ketene is conventionally carried out in a system which includes an absorber and at least one ketene scrubber. The process requires the use of both an absorber and at least one scrubber to achieve the desired overall conversion of ketene to acetic anhydride and subsequent carbon efficiency. These components and the use thereof, unfortunately, represent significant process expenses.

It has now been discovered that at least a portion of the vent gas from the absorber, instead of being directed to a costly ketene scrubber or series of scrubber towers, may be directed to a liquid ring vacuum compressor comprising a ring seal fluid comprising acetic acid. In one embodiment, a small number of liquid ring vacuum compressors are employed, e.g., less than 3 or less than 2. Preferably, a single liquid ring vacuum compressor is used. By utilizing only a few (or only one) liquid ring vacuum compressors, preferably one small compressor, which have acetic acid in the liquid ring seal fluid, at least a portion of the residual ketene in the vent gas may be reacted to form additional acetic anhydride. As such, overall ketene conversion and carbon efficiency are improved over a process that does not react the residual ketene. Also, overall ketene efficiency similar to or better than a process that utilizes a scrubber to react residual ketene can be achieved. Additionally, because only small-sized liquid ring vacuum compressor(s) are employed, the inventive systems are less expensive than conventional liquid ring vacuum compressor systems that employ either very large, high capacity liquid ring vacuum compressors or multiple smaller liquid ring vacuum compressors. It has also been discovered that when the concentration of acetic acid in the ring seal fluid is maintained at or within a specific range, improvements in ketene conversion are surprisingly achieved.

Generally speaking, a liquid ring vacuum compressor may employ a ring seal fluid that can react with components of the vapor stream that is being directed through the compressor. As a result, the liquid ring compressor may facilitate a reaction and yield a reaction product. In some cases, liquid ring vacuum compressor(s) may be used to conduct the acetic acid/ketene reaction. Conventionally, an absorber is not employed upstream of the liquid ring vacuum compressor(s) and, as a result, the ketene-containing stream that is fed to the liquid ring vacuum compressor(s) is significantly different than the vent stream of the present invention. As some examples of these differences, conventional ketene-containing streams are significantly larger in flow rate and comprise significantly higher concentrations of ketene, e.g., greater than 10 wt %, greater than 50 wt % or greater than 90 wt %. Conventional processes that utilize liquid ring vacuum compressor(s) require either a very large, high capacity liquid ring vacuum compressor or multiple smaller liquid ring vacuum compressors to provide an adequate vacuum source and to achieve reaction of the ketene stream fed thereto. Such configurations typically require significant capital expenditure. As such, the use of a liquid ring vacuum compressor(s) in combination with an absorber unit (which also requires significant capital expenditure) has not been and would not be contemplated by one skilled in the art.

It has now been found that the utilization of a liquid ring vacuum compressor with the absorber, as opposed to other vacuum sources such as a multi-stage eductor, provides suitable vacuum source required for operation of a low-pressure ketene-acetic anhydride process with less energy usage. In addition, the liquid ring vacuum compressor produces a reliable, constant pressure decomposition gas stream that may, in some embodiments, be sent to a fired-heater, e.g., an acetic acid cracking furnace. Also, the use of a liquid ring vacuum compressor further provides a low residence time and controlled low-temperature opportunity for capturing, mixing, and reaction of residue ketene gas contained in an absorber tower vent stream. In particular, relatively high fresh acetic acid feed rates in combination with the small liquid volume required for operation of the liquid ring vacuum compressor results in a low residence time and helps maintain a low concentration of ketene in the seal fluid liquid. Such low concentrations would not be present in conventional processes that do not employ an absorber in combination with the liquid ring vacuum compressor. Furthermore, the dilution of ketene, low residence time, and low temperature operation minimizes the formation of ketene derivatives, e.g., diketene, which are considered to be undesirable impurities.

Accordingly, in one embodiment, the present invention relates to a process for producing acetic anhydride. The inventive process comprises the step of carbonylating methanol and/or a methanol derivative with carbon monoxide to form acetic acid. Acetic acid is contacted with ketene to produce a crude acetic anhydride product stream and a vent stream comprising residual, unreacted ketene. In a preferred embodiment, acetic acid is pyrolyzed in cracking furnace to generate ketene gas. After separation of the ketene gas from a liquid stream comprising water and acetic acid, the ketene gas is contacted with liquid acetic acid to produce the crude acetic anhydride product stream and the vent stream. For example, the vent stream may comprise from 0.1 wt % to 10 wt % ketene, e.g., from 0.1 wt % to 8 wt % or from 1 wt % to 5 wt %. The vent stream of the present invention comprises significantly less ketene than would be fed to liquid ring vacuum compressor(s) of a conventional process, which would employ only liquid ring vacuum compressor(s) and would not employ an absorber in combination with the liquid ring vacuum compressor(s). Preferably, the acetic acid and ketene are reacted in an absorber column. In preferred embodiments, at least a portion of the unreacted ketene is directed to a liquid ring vacuum compressor, which comprises a ring seal fluid comprising acetic acid. Preferably, the process does not employ a ketene scrubber and the unreacted ketene is fed directly to the liquid ring vacuum compressor, although, in some embodiments, the unreacted ketene may be directed through heat exchanger equipment and/or additional pumping equipment before reaching the liquid ring vacuum compressor. As noted above, in some embodiments, surprising ketene conversions are achieved when the ring seal fluid comprises specific concentrations of acetic acid. The composition of the ring seal fluid is discussed in detail below. In one embodiment, the acetic acid acts as both a seal fluid and a reactant in the liquid ring vacuum compressor in embodiments of the present disclosure. Preferably, the unreacted ketene is contacted with the ring seal fluid to form additional acetic anhydride, e.g., a supplemental acetic anhydride product. As a result, the overall conversion of ketene to acetic anhydride of the inventive process is at least 95%, e.g., at least 97%, at least 98%, at least 99%, at least 99.5%, or at least 99.99%.

Acetic Acid

As noted above, in one embodiment, the inventive process includes the step of carbonylating methanol and/or a methanol derivative with carbon monoxide to form acetic acid. As used herein, the term "methanol derivative" refers to a compound that is derived from or formed from methanol. Examples of methanol derivatives include, but are not limited to, methyl acetate and dimethyl ether. The carbonylation of methanol proceeds according to the following equation:

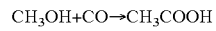

$$CH_3OH + CO \rightarrow CH_3COOH$$

The acetic acid used in connection with the process of this invention may be derived from any suitable source including natural gas, petroleum, coal, biomass, and so forth. In one embodiment, the acetic acid may be produced via methanol carbonylation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

In one optional embodiment, the acetic acid that is utilized in the acetic acid/ketene reaction comprises acetic acid and may also comprise other carboxylic acids, e.g., propionic acid, esters, and anhydrides, such as acetic anhydride, as well as acetaldehyde. In one embodiment, the acetic acid fed to the acetic acid/ketene reaction comprises "light-end" impurities, such as acetone and acetonitrile. In another embodiment, the acetic acid fed to the acetic acid/ketene reaction comprises propionic acid. For example, the acetic acid fed to the reaction may comprise less than 600 ppm propionic acid, e.g., less than 590 ppm, less than 575 ppm, less than 500 ppm, less than 400 ppm, or less than 300 ppm propionic acid in the acetic acid feed. The acetic acid fed to the reaction may be a cruder acetic acid feed stream, e.g., a less-refined acetic acid feed stream.

In one embodiment, acetic acid in vapor form may be taken directly as crude product from the flash vessel of a methanol carbonylation unit of the class described in U.S. Pat. No. 6,657,078, the entirety of which is incorporated herein by reference.

In another embodiment, at least a portion of the acetic acid that is fed to the acetic acid/ketene reaction may be provided by a recycle stream. For example, excess acetic acid that is fed to the acetic acid/ketene reaction may be recovered from the crude acetic anhydride product stream through various separation steps. The recovered acetic acid is then fed to the acetic acid/ketene reaction as a recycle stream. The acetic acid stream may comprise low amounts of acetic anhydride, and/or low amounts of water. In optional embodiments, the acetic acid recycle stream may further comprise impurities that are more volatile (i.e. have lower boiling points) that acetic anhydride. In such optional embodiments, the inventive process may comprise additional steps for purging these lower boiling point ("light-ends") impurities from the recycle stream. Although these impurities do not affect the acetic acid/ketene reaction, they may have an effect on the overall quality of the acetic anhydride product.

Ketene

Ketene can be prepared by various methods known in the art, most commonly by vapor phase pyrolysis (continuous cracking) of acetic acid in the presence of a catalyst at subatmospheric pressure. Suitable pyrolysis catalysts include, but are not limited to, triethyl phosphate, diammonium phosphate, monoammonium phosphate or other esters of phosphoric acid. In one embodiment, the pyrolysis catalyst may be added in an amount ranging from 0.1 to 0.5 wt % based on total weight of the feed. In some embodiments of the present invention, the pyrolysis is conducted at temperatures at or above 600° C., such as 650° C., 700° C., 750° C., 800° C., 850° C., 880° C., 900° C., 950° C. or 1100° C. In terms of ranges, the pyrolysis may be conducted at a temperature ranging from 600 to 1100° C., e.g., from 650 to 1000° C., from 700 to 1000° C., from 725 to 990° C., or from 740 to 900° C. In preferred embodiments, the pyrolysis is conducted at a temperature ranging from 600° C. to 650° C. In one embodiment, a neutralizing agent, such as ammonia, may be introduced to the reactor system after pyrolysis to neutralize the pyrolysis catalyst. The neutralizing agent also acts to retard recombination of the ketene with reacted acetic acid, and/or water formed during the reaction. Suitable neutralizing agents include, but are not limited to, ammonia, pyridine, aniline, or other suitable aliphatic amines.

In order to recover ketene by purification of the pyrolysis gas, condensable gas may be separated from the pyrolysis gas. Accordingly, in one embodiment of the present invention, the pyrolysis gas is rapidly cooled, and the ketene gas is recovered by separating the condensable component(s), e.g., $H_2O$, acetic acid, etc., from the pyrolysis gas. In embodiments where it is desired, the ketene gas may be further cooled by use of one or more condensers to, for example, 10° C. or less, to remove all but trace quantities of water and acetic acid from the recovered ketene.

Primary Reaction

As noted above, the inventive process, in one embodiment, further comprises the step of contacting ketene with acetic acid to produce a crude acetic anhydride product stream and a vent stream comprising unreacted ketene. In preferred embodiments, this step is performed in an absorber column. Ketene, in the vapor phase, and acetic acid, in the liquid phase, may be fed to the absorber column.

In one embodiment, the crude acetic anhydride product stream of the present invention comprises a significant portion of acetic anhydride. For example, the crude product stream may comprise at least 50 wt % acetic anhydride, e.g., at least 75 wt %, at least 80 wt %, at least 85 wt %, at least 90 wt %, or at least 95 wt %. In terms of ranges, the crude product stream may comprise from 1 to 50 wt % acetic anhydride, e.g., from 15 to 60 wt %, from 25 to 75 wt %, from 30 to 80 wt %, from 50 to 85 wt %, from 60 to 85 wt %, from 70 to 85 wt %, or from 75 to 95 wt %. In terms of upper limits, the crude product stream may comprise less than 95 wt % acetic anhydride, e.g., less than 90 wt % acetic anhydride, less than 85 wt % acetic anhydride, less than 80 wt % acetic anhydride, or less than 75 wt % acetic anhydride. In preferred embodiments, the crude product stream comprises at least 85 wt % acetic anhydride. The crude product stream may be further purification. In one embodiment, the crude product stream may be combined with acetic anhydride from the secondary reaction and the combined stream may be further purified.

In one embodiment, the crude acetic anhydride product stream of the present invention further comprises acetic acid. For example, the crude product stream may comprise at least 3 wt % acetic acid, at least 5 wt % acetic acid, at least 10 wt % acetic acid, at least 15 wt % acetic acid, or at least 20 wt % acetic acid. In terms of ranges, the crude product stream may comprise from 0.1 to 10 wt % acetic acid, from 2 to 15 wt % acetic acid, from 5 to 17 wt % acetic acid, or from 7 to 20 wt % acetic acid. In terms of upper limits, the crude product stream of the present invention may comprise less than 20 wt % acetic acid, less than 15 wt % acetic acid, less than 10 wt % acetic acid, or less than 5 wt % acetic acid.

In other embodiments, the crude acetic anhydride product stream may comprise propionic acid, acetic, acetic-propionic anhydride, propionic anhydride, acetone, diketene, diacetamide, acetonitrile, acetaldehyde, and mixtures thereof. Although the acetic acid feed and the ketene gas stream may contain very small concentrations of water, the crude acetic anhydride stream preferably does not contain measureable amounts of water.

In some embodiments, at least a portion of the crude acetic anhydride product stream may be hydrogenated to ethanol.

Exemplary compositional data for the crude product stream are shown in Table 1. Components other than those listed in Table 1 may also be present in the crude product stream.

TABLE 1

CRUDE ACETIC ANHYDRIDE PRODUCT STREAM COMPOSITIONS

| Component | Conc. (wt %) | Conc. (wt %) | Conc. (wt %) | Conc. (wt %) |
|---|---|---|---|---|
| Acetic Anhydride | 1 to 95 | 10 to 85 | 10 to 90 | 15 to 95 |
| Acetic Acid | 0.1 to 20 | 1 to 10 | 1 to 15 | 1 to 20 |
| Propionic Acid | 0.001 to 1 | 0.01 to 1 | 0.1 to 2 | 0.01 to 0.1 |
| Acetic Propionic Anhydride | 0.001 to 1 | 0.01 to 1 | 0.1 to 2 | 0.01 to 0.1 |

In one embodiment, the vent stream of the present invention comprises unreacted ketene. For example, the vent stream may comprise from 0.1 wt % to 10 wt % ketene, e.g., from 0.1 to 8 wt %, from 0.5 to 7 wt %, from 0.75 to 6 wt %, or from 1 to 5 wt % ketene. In terms of upper limits, the vent stream of the present invention comprises less than 10 wt % ketene, e.g., less than 9 wt % ketene, less than 8 wt % ketene, less than 7 wt % ketene, less than 6 wt % ketene, or less than 5 wt % ketene in the vent stream. In terms of lower limits, the vent stream of the present invention comprises at least 0.1 wt % ketene, e.g., at least 0.5 wt % ketene, at least 1 wt % ketene, at least 2 wt % ketene, at least 3 wt % ketene, or at least 5 wt % ketene in the vent stream.

In one embodiment, the vent stream further comprises acetic acid and/or acetic anhydride, optionally in the vapor phase. For example, the vent stream of the present invention may comprise acetic acid and/or acetic anhydride in an amount ranging from 10 wt % to 60 wt %, e.g., from 20 wt % to 50 wt %, from 25 wt % to 45 wt %, or from 30 wt % to 40 wt %. In terms of upper limits, the vent stream of the present invention may comprise less than 40 wt % acetic acid and/or acetic anhydride, e.g., less than 60 wt %., less than 50 wt %, less than 45 wt %, or less than 40 wt % acetic acid and acetic anhydride vapor. In terms of lower limits, the vent stream of the present invention may comprise at least 10 wt % acetic acid and/or acetic anhydride, e.g., at least 20 wt %, at least 25 wt %, at least 30 wt %, or at least 35 wt %.

Exemplary compositional data for the vent stream are shown below in Table 2. Components other than those listed in Table 2 may also be present in the vent stream.

TABLE 2

VENT STREAM COMPOSITIONS

| Component | Conc. (wt %) | Conc. (wt %) | Conc. (wt %) | Conc. (wt %) |
|---|---|---|---|---|
| Acetic Anhydride/Acetic Acid Vapor | 10 to 60 | 20 to 50 | 25 to 45 | 30 to 40 |
| Ketene | 0.01 to 10 | 0.05 to 10 | 0.1 to 10 | 1 to 15 |
| Decomposition Gas | 40 to 80 | 45 to 75 | 50 to 80 | 50 to 70 |

The decomposition gas, in some embodiments, comprises carbon monoxide, carbon dioxide, methane, ethylene, propadiene, nitrogen and other olefins and hydrocarbons, and mixtures thereof.

As indicated above, in preferred embodiments, the contacting of ketene with acetic acid, preferably, may be performed in an absorber column. The formation of acetic anhydride from the reaction between acetic acid and ketene is an exothermic reaction ($\Delta H = -63$ kJ/gmol).

In one embodiment, the absorber column is operated at lower than atmospheric pressure. For example, the top of the absorber column (vent) pressure is from 3 KPa to 100 KPa, e.g., from 30 KPa to 90 KPa, or from 40 KPa to 80 KPa, or from 40 KPa to 70 KPa, or from 50 KPa to 60 KPa. Without being bound by theory, with respect to operating temperature, there is generally a trade-off between absorber column operating temperature and its effect on acetic acid/ketene reaction kinetics, versus the vapor pressure of acetic acid. In particular, although increasing the absorber column operating temperature increases the rate of the acetic acid/ketene reaction, it also increases the amount of acetic acid and acetic anhydride that is in the vapor phase (i.e. by increasing their partial pressures). In one embodiment, the overhead operating temperature of the absorber column ranges from 10° C. to 80° C., e.g., from 35 to 55° C. In one embodiment, the temperature of the vent stream exiting the reactor system (e.g., absorber column) of the present invention ranges from 10° C. to 80° C., e.g., from 20° C. to 70° C. or from 30° C. to 60° C.

In one embodiment, the use of the liquid ring vacuum compressor in combination with the absorber surprisingly and unexpectedly provides for high overall ketene efficiency. For example, the overall ketene efficiency may be at least 95%, e.g., at least 97%, at least 98%, at least 99%, at least 99.5%, or at least 99.99%. In preferred embodiments, the overall ketene efficiency is 99.5%, meaning that only approximately 0.5% of the ketene fed to the system leaves as unreacted ketene. In other words, a reactor system with 99.5% ketene efficiency effectively translates to having 99.5% of the ketene fed to the reactor converted into product. In terms of ranges, the overall ketene efficiency may range from 95% to 99.99%, e.g., from 96 to 99.99%, from 97 to 99.99%, from 98 to 99.5%, from 98.9 to 99.5%, or from 99 to 99.99%. In terms of upper limits, the overall ketene efficiency of the process of the present invention may be less than 99.99%, e.g., less than 99.95%, less than 99.5%, less than 99%, or less than 98.5%.

Conversion of Unreacted Ketene

In one embodiment, the inventive process comprises directing at least a portion of the vent stream to a liquid ring vacuum compressor comprising a ring seal fluid comprising acetic acid. As stated above, in some embodiments, acetic acid acts as a sealer and/or as a reactant. Preferably, the unreacted ketene in the vent stream is allowed to react with acetic acid to yield supplemental acetic anhydride product. In some embodiments, the ring seal fluid comprises greater than 10 wt % acetic acid, e.g., greater than 12 wt % acetic acid, greater than 15 wt % acetic acid, greater than 20 wt % acetic acid, greater than 25 wt % acetic acid, or greater than 30 wt % acetic acid. Preferably, the acetic acid in the ring seal fluid is maintained at a concentration greater than 10 wt %. In terms of ranges, the acetic acid concentrations in the ring seal fluid can range from about 10 wt % to 90 wt %, e.g., from about 15 wt % to 70 wt %, from about 20 wt % to 60 wt %, or from about 25 wt % to 55 wt %. In the specific configuration of the present invention, it has been discovered that maintaining the acetic acid concentration within theses ranges provides for improvements in (residual) ketene conversion. In one embodiment, the upper range for acetic acid concentrations in the liquid ring seal fluid may be related to the freezing point of the ring seal fluid, as it is used in the specific configuration of the present invention. In some embodiments, the ring seal fluid further comprises acetic anhydride. For example, acetic anhydride may be present in the ring seal fluid in an amount ranging from 20 wt % to 95 wt %, e.g., from 25 wt % to 75 wt % or from 30 wt % to 60 wt %. In terms of upper limits, the ring seal fluid may comprise less than 95 wt % acetic anhydride, e.g., less than 75 wt % or less than 60 wt %. In terms of lower limits, the ring seal fluid may comprise greater than 20 wt % acetic anhydride, e.g., greater than 25 wt % or greater than 30 wt %. In one embodiment, a weight ratio of acetic acid to acetic anhydride in the ring seal fluid may range from 10:1 to 1:10, e.g., from 5:1 to 1:5 or from 2:1 to 1:2. Preferably, the weight ratio of acetic acid to acetic anhydride in the ring seal fluid is about 1:1. In optional embodiments, the ring seal fluid may further comprise low boiling point solvents, such as acetone, which can build-up in the liquid ring seal fluid. Preferably, the presence of such low boiling point solvents in the ring seal fluid is minimized or eliminated, in order to prevent any negative impact on the effectiveness of the vacuum compressor.

In one embodiment, the operating pressure(s) of the liquid ring vacuum compressor ranges from 3 MPa to 100 MPa, e.g., form 5 MPa to 95 MPa, from 10 MPa to 80 MPa, or from 15 MPa to 75 MPa. In terms of upper limits, the liquid ring vacuum compressor may operate at a pressure less than 100 MPa, e.g., less than 98 MPa, less than 95 MPa or less than 90 MPa. In terms of lower limits, the liquid ring vacuum compressor may operate at a pressure greater than 3 MPa, e.g., greater than 5 MPa or greater than 10 MPa.

In some embodiments, the operating temperature(s) of the liquid ring vacuum compressor ranges from 0° C. to 75° C., e.g., from 10° C. to 65° C. or from 20° C. to 60° C. In terms of upper limits, the liquid ring vacuum compressor may operate at a temperature less than 75° C., e.g., less than 65° C. or less than 60° C. In terms of lower limits, the liquid ring vacuum compressor may operate at a temperature greater than 0° C., e.g., greater than 10° C. or greater than 20° C.

The inventive process, in one embodiment, comprises the step of contacting the unreacted ketene in at least a portion of the vent stream with the ring seal fluid to form supplemental acetic anhydride product. As a result, overall ketene efficiency is improved as indicated above.

Preferred embodiments of the inventive process maintain a ring seal fluid composition at a minimum acetic anhydride concentration level such that the amount of diketene formed in the liquid ring seal vacuum compressor is kept at a minimum. This, in turn, eliminates or significantly minimizes the amount of diketene present in the crude acetic anhydride produced by the inventive process, and beneficially results in lesser amounts of diketene in acetic anhydride purified by distillation to produce high quality product.

The use of the liquid ring vacuum compressor eliminates costly equipment requirements of conventional acetic anhydride production processes. As noted above, conventional processes typically require scrubber towers to accomplish reacting unreacted ketene from the reactor system, to yield additional acetic anhydride product. It has been surprisingly found that the simultaneous removal of a scrubber tower and incorporation of a liquid ring vacuum compressor according to the inventive process accomplished superior ketene efficiency at reduced operating costs, and also may minimize undesirable impurities otherwise present in crude acetic anhydride product. In one embodiment, the liquid ring vacuum compressor is operated at a lower liquid seal fluid circulation rate, as compared to conventional liquid ring vacuum compressors, For example the liquid seal fluid circulation rate may range from 150 kg/minute to 250 kg/minute, e.g., from 175 kg/minute to 225 kg/minute.

The product stream exiting the liquid ring vacuum compressor comprises a supplemental acetic anhydride product. In one embodiment, the product stream exiting the liquid ring vacuum compressor comprises acetic anhydride. In one embodiment the product stream exiting the liquid ring vacuum compressor comprises acetic acid. In some embodiments, the supplemental acetic anhydride product comprises low amounts of ketene, e.g., less than 0.5 wt % ketene, less than 0.4 wt % ketene, less than 0.3 wt % ketene, or less than 0.2 wt %. In some embodiments, the product stream exiting the liquid ring vacuum compressor further comprises decomposition gas.

Exemplary compositional data for the product stream exiting the liquid ring vacuum compressor are shown below in Table 3. Components other than those listed in Table 3 may also be present in the exit stream from the liquid ring vacuum compressor. For example, the exit stream may also comprise acetone and acetonitrile.

TABLE 3

COMPOSITIONS IN STREAM EXITING THE LIQUID RING VACUUM COMPRESSOR

| Component | Conc. (wt %) | Conc. (wt %) | Conc. (wt %) | Conc. (wt %) |
|---|---|---|---|---|
| Acetic Anhydride | 20 to 95 | 25 to 80 | 30 to 70 | 35 to 65 |
| Acetic Acid | 20 to 95 | 25 to 80 | 30 to 70 | 35 to 65 |
| Decomposition Gas | 0.1 to 10 | 0.5 to 8 | 0.8 to 5 | 1 to 3 |
| Ketene | 0.01 to 1.0 | 0.01 to 0.6 | 0.1 to 0.5 | 0.1 to 0.4 |

In some embodiments, the product stream exiting the liquid ring vacuum compressor may be further processed. In one embodiment, the inventive process may further comprise a step of separating the product stream exiting the liquid ring vacuum compressor to form a recycle stream comprising acetic acid and a decomposition gas stream. In one embodiment, the product stream exiting the liquid ring vacuum compressor is directed to a seal fluid vessel (knock-out pot) to effect the separation into a recycle stream and a decomposition gas stream. In some embodiments, decomposition gas is separated from an acetic acid/acetic anhydride mixture entering the seal fluid vessel. In some embodiments, the decomposition gas is burned for fuel value.

In other embodiments, the product stream exiting the liquid ring vacuum compressor is directed to a seal fluid vessel (knock-out put) that is equipped with a final decomposition gas condenser that gravity drains any condensed liquid comprising acetic acid and/or acetic anhydride into the seal fluid vessel. For these embodiments, this provides a low dew point decomposition gas stream that, beneficially, can be used as a fuel source for steam production and/or direct-fired acetic acid cracking furnaces.

In some embodiments, at least a portion of the recycle stream comprising acetic acid is recycled to back to the liquid ring vacuum compressor to supply additional acetic acid to the compressor. In some embodiments where at least a portion of the recycle stream is recycled to the liquid ring vacuum compressor, the liquid ring vacuum compressor may be operated such that a weight ratio of the at least a portion of the liquid recycle stream to the vaporous vent stream ranges from 40:1 to 130:1, e.g., from 50:1 to 120:1, from 60:1 to 110:1, or from 65:1 to 105:1.

In some embodiments, at least a portion of the recycle stream comprising acetic acid is recycled back to the reaction unit. In some embodiments where at least a portion of the recycle stream is recycled to the reaction unit, the reaction unit, e.g., the absorber column, may be operated such that a weight ratio of the at least a portion of the liquid recycle stream to the vaporous ketene feed stream ranges from 70:1 to 130:1, e.g., from 80:1 to 125:1, from 90:1 to 110:1, or from 95:1 to 100:1. In preferred embodiments, the recycle stream to ketene inlet stream weight ratio is about 100:1.

In some embodiments, at least a portion of the recycle stream is recycled back to the liquid ring vacuum compressor. In some embodiments, at least a portion of the recycle stream is recycled back to the reaction unit. For some embodiments, any one of the above-described recycle streams of the inventive process (e.g., acetic acid recycle stream fed to the compressor, acetic anhydride recycle stream fed to the reactor) may utilize a brine cooled heat exchanger to cool the recycle stream.

Exemplary compositional data for the acetic acid/acetic anhydride recycle stream are shown below in Table 4. Components other than those listed in Table 4 may also be present in the recycle stream.

TABLE 4

ACETIC ACID/ACETIC ANHYDRIDE LIQUID RECYCLE STREAM COMPOSITIONS

| Component | Conc. (wt %) | Conc. (wt %) | Conc. (wt %) | Conc. (wt %) |
|---|---|---|---|---|
| Acetic Anhydride | 20 to 95 | 25 to 80 | 30 to 70 | 35 to 65 |
| Acetic Acid | 20 to 95 | 25 to 80 | 30 to 70 | 35 to 65 |
| Acetone | 0.01 to 15 | 1 to 12 | 2 to 10 | 5 to 9 |
| Acetonitrile | 0.01 to 15 | 1 to 12 | 2 to 10 | 5 to 9 |

The process according to one embodiment of the present invention will now be described in relation to FIG. 1.

FIG. 1 is a flow diagram depicting process 100 for producing acetic anhydride according to one embodiment of the present invention. Process 100 comprises primary reaction zone 101 and secondary reaction zone 104. Reaction zone 101 comprises reaction unit 103. In some embodiments, secondary reaction zone 104 comprises both reaction and separation equipment. With reference to FIG. 1, ketene is fed to the reaction unit 103 via line 102. Although not illustrated, acetic acid may also be directly fed or combined and jointly fed to the reaction unit 103 via the same stream 102 as shown in FIG. 1. The temperature of the ketene feed stream 102 is preferably from −5° to 25° C., e.g., from 0 to 15° C., or from 5 to 10° C. In preferred embodiments, reaction unit 103 comprises an absorber, although other suitable reaction units may be employed to facilitate the ketene/acetic acid reaction.

In reaction unit 103, acetic acid and ketene are reacted to produce a crude acetic anhydride product stream, which exits reaction unit 103 via line 106. Although FIG. 1 shows the crude product stream being withdrawn from the bottom of reaction unit 103, the crude product stream may be withdrawn from any portion of reaction unit 103. Exemplary composition ranges for the crude product stream are shown in Table 1 above.

At least a portion of crude acetic anhydride product stream may be recycled to reaction unit 103 via line 120. In one embodiment, line 120 may be combined with acetic acid and returned to reaction unit 103. For example, line 120 may be combined with optional acetic acid feed 108 and directed to reaction unit 103. As another example, line 120 may be combined with a recycle stream, e.g., a recycle stream from secondary reaction zone 104 and directed to reaction unit 103. Resultant combined stream 119 may then be fed to heat exchanger, e.g., cooling water or a brine cooled heat exchanger, 107 prior to being re-introduced to reaction unit 103 via line 118.

Unreacted ketene from reaction unit 103 flows from the top of reaction unit 103 as an overhead vent stream via line 105. Exemplary composition ranges for the vent stream are shown above in Table 2. The vent stream 105 and the unreacted ketene therein passes to liquid ring vacuum compressor 109. Liquid ring vacuum compressor 109 comprises a ring seal fluid (not shown) comprising acetic acid. The ketene from vent stream 105 reacts with the acetic acid to form additional acetic anhydride product. At least a portion of the acetic acid in the ring seal fluid is provided by a recycle stream, e.g., a recycle stream from secondary reaction zone 104. Liquid ring vacuum compressor 109 forms outlet stream 110, which comprises additional acetic anhydride.

Supplemental product stream 110 exits liquid ring vacuum compressor 109. In addition to acetic anhydride, supplemental product stream 110 comprises acetic acid, decomposition gas and very small amounts of ketene (if any). Exemplary composition ranges for supplemental product stream 110 are shown in Table 3 above. Supplemental product stream 110 is directed to seal fluid vessel 111. In one embodiment, seal fluid vessel 111 is a knock-out pot. Preferably, additional acetic acid is fed to seal fluid vessel 111 via line 113. Seal fluid vessel 111 separates the contents of supplemental product stream 110 to form a decomposition gas in line 112 and an acetic acid/acetic anhydride mixture (optionally comprising trace amounts of ketene) in line 114.

Decomposition gas exits seal fluid vessel 111 in line 112, e.g., separate from the acetic acid/acetic anhydride mixture recycle stream in line 114. Although FIG. 1 shows decomposition gas being withdrawn from the top of seal fluid vessel 111, the decomposition gas stream may be withdrawn from other portions of seal fluid vessel 111. Decomposition gas stream 112 can be further cooled to lower the dew point of this stream.

The recycle stream exits seal fluid vessel 111 via line 114. At least a portion of line 114 is fed to brine cooled heat exchanger 115. At least a portion of the cooled recycle stream exits heat exchanger 115 and is fed into liquid ring vacuum compressor 109 via line 116. In one embodiment, the weight ratio of liquid in line 116 to the vaporous vent stream in line 105 is as described above. Although FIG. 1 shows recycle stream 114 being withdrawn from the bottom of seal fluid vessel 111, the liquid acetic acid/acetic anhydride mixture stream may be withdrawn from any portion of seal fluid vessel 111. At least a portion of recycle stream 114 is recycled to reaction unit 103, via line 117, which in some embodiments, may be considered a supplemental acetic anhydride product stream. In one embodiment, the weight ratio of liquid in line 118 to the vaporous ketene feed in line 102 is as described above. Exemplary composition ranges for the acetic acid/acetic anhydride recycle stream are shown in Table 4 above. The acetic acid/acetic anhydride mixture stream is recycled to reaction unit 103 in line 117, and, in one embodiment, can also be withdrawn from line 116 after the brine-cooled recirculation cooler 115.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing acetic anhydride, the process comprising the steps of:
    (a) carbonylating methanol and/or a methanol derivative with carbon monoxide to form acetic acid;
    (b) contacting ketene with the acetic acid to produce a crude acetic anhydride product stream comprising acetic anhydride and a vent stream comprising:
    unreacted ketene; and
    from 10 wt % to 60 wt % acetic acid and/or acetic anhydride vapor;
    (c) directing at least a portion of the vent stream to a liquid ring vacuum compressor comprising a ring seal fluid comprising acetic acid; and
    (d) contacting the unreacted ketene in the at least a portion of the vent stream with the ring seal fluid to form a supplemental acetic anhydride product.

2. The process of claim 1, wherein step (b) is performed in an absorber column.

3. The process of claim 1, wherein the vent stream comprises from 0.1 wt % to 10 wt % ketene.

4. The process of claim 1, wherein the vent stream comprises from 20 wt % to 40 wt % acetic acid and/or acetic anhydride vapor.

5. The process of claim 1, wherein the ring seal fluid comprises from 10 wt % to 90 wt % acetic acid.

6. The process of claim 1, wherein the process does not employ a ketene scrubber unit.

7. The process of claim 1, wherein the supplemental acetic anhydride product comprises less than 0.5 wt % ketene.

8. The process of claim 1, wherein overall ketene conversion to acetic anhydride is at least 98%.

9. The process of claim 1, further comprising the step of:
    (e) separating the supplemental acetic anhydride product to form a recycle stream comprising acetic acid and a decomposition gas stream.

10. The process of claim 9, further comprising the step of:
    (f) recycling at least a portion of the recycle stream to the liquid ring vacuum compressor.

11. The process of claim 10, wherein a weight ratio of the at least a portion of the recycle stream from step (f) to the at least a portion of the vent stream ranges from 40:1 to 130:1.

12. The process of claim 9, wherein step (b) is conducted in a reaction unit.

13. The process of claim 12, further comprising the step of:
    (g) recycling at least a portion of the recycle stream to the reaction unit.

14. The process of claim 13, wherein a weight ratio of the at least a portion of the recycle stream from step (g) to ketene feed ranges from 70:1 to 130:1.

15. The process of claim 9, wherein the recycle stream further comprises acetic anhydride.

16. The process of claim 1, wherein step (b) is performed in an absorber column and wherein no additional reaction units are present in the process.

17. The process of claim 16, wherein overall ketene conversion is at least 98%.

18. The process of claim 1, wherein at least a portion of the ketene in step (b) is obtained by:
    pyrolyzing acetic acid at a high temperature to produce a crude ketene vapor stream comprising ketene, acetic acid and water; and separating the crude ketene vapor stream to produce at least a ketene feed stream and an aqueous stream, wherein the pyrolyzing is conducted at a temperature ranging from 600° C. to 650° C.

19. The process of claim 1, wherein the ring seal fluid comprises greater than 10 wt % acetic acid.

20. A process for producing acetic anhydride, the process comprising the steps of:
   (a) carbonylating methanol and/or a methanol derivative with carbon monoxide to form acetic acid;
   (b) contacting ketene with the acetic acid to produce a crude acetic anhydride product stream comprising acetic anhydride and a vent stream comprising:
   unreacted ketene; and
   from 10 wt % to 60 wt % acetic acid and/or acetic anhydride vapor;
   (c) reacting at least a portion of the unreacted ketene in the vent stream with acetic acid in a liquid ring vacuum compressor to form supplemental acetic anhydride.

21. A process for producing acetic anhydride, the process comprising the steps of:
   (a) providing an acetic acid stream comprising acetic acid and less than 600 ppm propionic acid;
   (b) contacting ketene with the acetic acid to produce a crude acetic anhydride product stream comprising acetic anhydride and a vent stream comprising:
   unreacted ketene; and
   from 10 wt % to 60 wt % acetic acid and/or acetic anhydride vapor;
   (c) directing at least a portion of the vent stream to a liquid ring vacuum compressor comprising a ring seal fluid comprising acetic acid; and
   (d) contacting the unreacted ketene in the at least a portion of the vent stream with the ring seal fluid to form a supplemental acetic anhydride product.

22. The process of claim 21, wherein step (b) is performed in an absorber column.

* * * * *